(12) United States Patent
Kopp

(10) Patent No.: US 11,446,101 B2
(45) Date of Patent: Sep. 20, 2022

(54) SURGICAL ROBOTIC ASSEMBLIES AND INSTRUMENT ADAPTERS THEREOF

(71) Applicant: Covidien LP, Mansfield, MA (US)

(72) Inventor: Brock Kopp, Boulder, CO (US)

(73) Assignee: Covidien LP, Mansfield, MA (US)

( * ) Notice: Subject to any disclaimer, the term of this patent is extended or adjusted under 35 U.S.C. 154(b) by 315 days.

(21) Appl. No.: 16/857,398

(22) Filed: Apr. 24, 2020

(65) Prior Publication Data

US 2020/0246091 A1 Aug. 6, 2020

Related U.S. Application Data

(63) Continuation of application No. 15/758,961, filed as application No. PCT/US2016/052778 on Sep. 21, 2016, now Pat. No. 10,639,111.

(Continued)

(51) Int. Cl.
*A61B 34/30* (2016.01)
*A61B 34/37* (2016.01)
(Continued)

(52) U.S. Cl.
CPC ........ *A61B 34/30* (2016.02); *A61B 17/07207* (2013.01); *A61B 17/285* (2013.01);
(Continued)

(58) Field of Classification Search
CPC ........... A61B 2017/00486; A61B 2017/00477; A61B 2017/00398; A61B 2017/00115;
(Continued)

(56) References Cited

U.S. PATENT DOCUMENTS 7,793,812 B2 9/2010 Moore et al.
8,602,288 B2 12/2013 Shelton, IV et al.
(Continued)

FOREIGN PATENT DOCUMENTS

EP 2612616 A1 7/2013
EP 2668910 A2 12/2013
(Continued)

OTHER PUBLICATIONS

Japanese Office Action dated Sep. 27, 2021 corresponding to counterpart Patent Application JP 2020-195735.
(Continued)

*Primary Examiner* — Jocelin C Tanner
(74) *Attorney, Agent, or Firm* — Carter, DeLuca & Farrell LLP

(57) ABSTRACT

An instrument adapter includes a housing, a drive member, a nut, and a shaft assembly. The nut is threadedly coupled to the drive member and axially movable relative thereto. The shaft assembly includes a shaft and a link. The shaft extends distally from the housing and is configured to be operably coupled to an end effector. The link has a proximal end movably coupled to the nut and a distal end configured to selectively lock the end effector to the shaft assembly. The link is movable between a proximal non-locking position, and a distal locking position. The nut is movable between a first position along the drive member, in which the nut resists proximal movement of the link from the distal position to the proximal position, and a second position, in which the nut does not resist proximal movement of the link from the distal position to the proximal position.

20 Claims, 6 Drawing Sheets

Related U.S. Application Data

(60) Provisional application No. 62/232,518, filed on Sep. 25, 2015.

(51) Int. Cl.
*A61B 17/072* (2006.01)
*A61B 34/00* (2016.01)
*A61B 34/35* (2016.01)
*A61B 17/285* (2006.01)
*A61B 17/00* (2006.01)

(52) U.S. Cl.
CPC .............. *A61B 34/25* (2016.02); *A61B 34/35* (2016.02); *A61B 34/37* (2016.02); *A61B 2017/00115* (2013.01); *A61B 2017/00398* (2013.01); *A61B 2017/00477* (2013.01); *A61B 2017/00486* (2013.01)

(58) Field of Classification Search
CPC ......... A61B 34/37; A61B 34/35; A61B 34/30; A61B 34/25; A61B 17/285; A61B 17/07207
See application file for complete search history.

(56) References Cited

U.S. PATENT DOCUMENTS

| | | | |
|---|---|---|---|
| 8,998,058 | B2 | 4/2015 | Moore et al. |
| 10,136,887 | B2 | 11/2018 | Shelton, IV et al. |
| 10,542,984 | B2 | 1/2020 | Nicholas et al. |
| 10,639,111 | B2 | 5/2020 | Kopp |
| 2004/0267254 | A1* | 12/2004 | Manzo ................. A61B 18/14 606/49 |
| 2006/0074415 | A1* | 4/2006 | Scott ................. A61B 18/1445 606/45 |
| 2006/0278680 | A1 | 12/2006 | Viola et al. |
| 2009/0108048 | A1 | 4/2009 | Zemlok et al. |
| 2009/0270892 | A1 | 10/2009 | Arcenio |
| 2011/0155786 | A1 | 6/2011 | Shelton, IV |
| 2012/0116416 | A1 | 5/2012 | Neff et al. |
| 2012/0259338 | A1 | 10/2012 | Carr et al. |
| 2013/0217967 | A1 | 8/2013 | Mohr et al. |
| 2013/0324978 | A1 | 12/2013 | Nicholas et al. |
| 2014/0012237 | A1* | 1/2014 | Pribanic ................. A61B 34/76 606/1 |
| 2014/0039519 | A1 | 2/2014 | Inoue et al. |
| 2014/0207182 | A1 | 7/2014 | Zergiebel et al. |
| 2014/0305988 | A1 | 10/2014 | Boudreaux et al. |
| 2014/0305990 | A1 | 10/2014 | Shelton, IV et al. |

FOREIGN PATENT DOCUMENTS

| | | |
|---|---|---|
| JP | 2008093430 A | 4/2008 |
| JP | 2009106752 A | 5/2009 |
| JP | 2013034859 A | 2/2013 |
| JP | 2014233632 A | 12/2014 |
| JP | 2015003017 A | 1/2015 |

OTHER PUBLICATIONS

Japanese Office Action dated Aug. 7, 2020 corresponding to counterpart Patent Application JP 2018-513499.
International Search Report and Written Opinion to counterpart Int'l Appln. No PCT/US2016/052778 dated Jan. 3, 2017.
Extended European Search Report dated Apr. 26, 2019 corresponding to counterpart Patent Application EP 16849460.7.
Australian Examination Report No. 1 dated Jun. 5, 2020 corresponding to counterpart Patent Application AU 2016326367 (attached).
Indian Office Action dated Mar. 26, 2021 corresponding to counterpart Patent Application IN 201817009245.
Australian Examination Report No. 1 dated Nov. 12, 2020 corresponding to counterpart Patent Application AU 2020220108.

* cited by examiner

SURGICAL ROBOTIC ASSEMBLIES AND INSTRUMENT ADAPTERS THEREOF

CROSS-REFERENCE TO RELATED APPLICATIONS

This application is a continuation application of U.S. patent application Ser. No. 15/758,961, filed Mar. 9, 2018 (now U.S. Pat. No. 10,639,111), which is a U.S. National Stage Application filed under 35 U.S.C. § 371(a) of International Patent Application Serial No. PCT/US2016/052778, filed Sep. 21, 2016, which claims the benefit of and priority to U.S. Provisional Patent Application Ser. No. 62/232,518, filed Sep. 25, 2015, the entire disclosure of each of which is incorporated by reference herein.

BACKGROUND

Robotic surgical systems have been used in minimally invasive medical procedures. Some robotic surgical systems included a console supporting a surgical robotic arm and a surgical instrument, having at least one end effector (e.g., forceps or a grasping tool), mounted to the robotic arm. The robotic arm provided mechanical power to the surgical instrument for its operation and movement.

Robotic surgical systems supported surgical instruments that were configured to couple to a variety of types of end effectors by enabling these end effectors to be readily exchanged during a surgical procedure. Typically, this exchange of end effectors was performed by manually detaching the end effector from the remainder of the surgical instrument without detaching the instrument drive unit from the surgical instrument. This often meant that end effectors could be detached from the surgical instrument by a clinician inadvertently by hitting the wrong button or switch.

There is a need for interchanging end effectors on a surgical instrument while preventing inadvertent removal of the end effector from the surgical instrument during the end effector exchange process.

SUMMARY

In accordance with an aspect of the present disclosure, an instrument adapter is provided. The instrument adapter is configured to interconnect a drive mechanism and an end effector. The instrument adapter transmits driving forces from the drive mechanism to the end effector for actuating the end effector. The instrument adapter includes a housing, a drive member, a nut, and a shaft assembly. The drive member is disposed within the housing, and the nut is threadedly coupled to the drive member and axially movable relative thereto. The shaft assembly includes a shaft and a link. The shaft has a proximal end coupled to the housing and a distal end configured to be operably coupled to the end effector. The link has a proximal end movably coupled to the nut and a distal end configured to selectively lock the end effector to the shaft assembly. The link is movable between a proximal non-locking position, and a distal locking position. The nut is movable between first and second positions along the drive member. In the first position, the nut resists proximal movement of the link from the distal position to the proximal position. In the second position, the nut does not resist proximal movement of the link from the distal position to the proximal position.

In some embodiments, the proximal end of the link may include a longitudinal slot formed therein. The nut may have a projection disposed within the longitudinal slot of the link such that when the nut is in the first position, the projection of the nut is engaged with a distal end surface of the longitudinal slot. When the nut is in the second position, the projection of the nut may be disposed adjacent a proximal end surface of the longitudinal slot.

It is contemplated that the nut may be movable to a third position along the drive member, located proximally of the first and second positions. The nut may effect proximal movement of the link for unloading the end effector upon the nut moving to the third position.

It is envisioned that the nut may be keyed to the housing such that rotation of the drive member moves the nut along the drive member between the first and second positions.

In some aspects, the link may be resiliently biased toward the distal position.

In some embodiments, the distal end of the link may include an extension configured for locking engagement with a lug of a surgical loading unit upon insertion and rotation of the surgical loading unit into the shaft assembly. The distal end of the shaft may include a cap defining a cutout configured for receipt of the extension of the link when the link is in the distal position. In the distal position, the extension of the link and the cutout of the cap may cooperatively define an enclosure for retaining the lug of the surgical loading unit.

It is contemplated that the housing may further include an input drive coupler non-rotatably coupled to a proximal end of the drive member. The input drive coupler may be configured to be rotated by a motor of the drive mechanism.

It is envisioned that the housing may define a window therein. The nut may include a tab disposed adjacent the window for manual movement of the nut to the second position.

In another aspect of the present disclosure, an electromechanical surgical instrument for connection to a drive mechanism is provided. The electromechanical surgical instrument includes a surgical loading unit and an instrument adapter. The surgical loading unit includes an elongate portion having a proximal end and a distal end, and an end effector extending from the distal end of the elongate portion. The instrument adapter includes a housing, a drive member, a nut, and a shaft assembly. The drive member is disposed within the housing, and the nut is threadedly coupled to the drive member and axially movable relative thereto. The shaft assembly extends distally from the housing and includes a shaft and a link. The shaft has a proximal end coupled to the housing and a distal end configured to be operably coupled to the proximal end of the elongate portion of the surgical loading unit. The link has a proximal end movably coupled to the nut and a distal end configured to selectively lock the surgical loading unit to the shaft assembly. The link is movable between a proximal non-locking position, and a distal locking position. The nut is movable between first and second positions along the drive member. In the first position, the nut resists proximal movement of the link from the distal position to the proximal position. In the second position, the nut does not resist proximal movement of the link from the distal position to the proximal position.

In another aspect of the present disclosure, a robotic surgical assembly is provided. The robotic surgical assembly includes a surgical robotic arm a surgical loading unit, and an instrument adapter. The surgical robotic arm supports a drive mechanism including a motor. The surgical loading unit includes an elongate portion having a proximal end and a distal end, and an end effector extending from the distal end of the elongate portion. The instrument adapter includes a housing, a drive member, a nut, and a shaft assembly. The housing is configured to be coupled to the surgical robotic arm. The drive member is disposed within the housing, and the nut is threadedly coupled to the drive member and axially movable relative thereto. The shaft assembly includes a shaft and a link. The shaft has a proximal end coupled to the housing and a distal end configured to be operably coupled to the proximal end of the elongate portion of the surgical loading unit. The link has a proximal end movably coupled to the nut and a distal end configured to selectively lock surgical loading unit to the shaft assembly. The link is movable between a proximal non-locking position, and a distal locking position. The nut is movable between first and second positions along the drive member. In the first position, the nut resists proximal movement of the link from the distal position to the proximal position. In the second position, the nut does not resist proximal movement of the link from the distal position to the proximal position.

In some embodiments, the drive mechanism may be configured to automatically move the nut from the second position to the first position upon the end effector being disposed adjacent a patient.

According to another aspect of the present disclosure, an instrument adapter, detachably coupleable to an instrument drive unit and an end effector, is provided. The instrument adapter includes a drive member coupled to an output of the instrument drive unit when the instrument adapter is coupled to the instrument drive unit; a shaft having a coupling interface corresponding to that of the end effector; a link movable between a block position in which the link prevents attaching or detaching of the end effector to the shaft through the coupling interface and an unblock position in which the link does not prevent said attaching or detaching; and a lock driven by the drive member and coupled to the link.

The lock drivable to a plurality of states including a first state in which the link is driven to the unblock position; a second state in which the lock is driven to a position in which the link is manually movable in at least one direction between the block and unblock positions; and a third state in which the link is driven to the block position.

In some embodiments, an instrument adapter may be detachably couplable to an instrument drive unit and an end effector. The instrument adapter may include a drive member configured to be coupled to an output of the instrument drive unit. The instrument adapter may also include a shaft having a distal end configured to be coupled to the end effector. The instrument adapter may also include a link that is movable between a block position in which the link prevents attaching or detaching of the end effector to the distal end of the shaft and an unblock position in which the link does not prevent attaching or detaching of the end effector to the distal end of the shaft. The instrument adapter may also include a lock driven by the drive member and coupled to the link. The lock may be drivable by the drive member to different positions or states. A first state may be one in which the link is in the unblock position. A second state may be one in which the lock and/or link are in a position in which the link is manually movable in at least one direction between the block and unblock positions, and a third state in which the link is in the block position.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Figure 1:
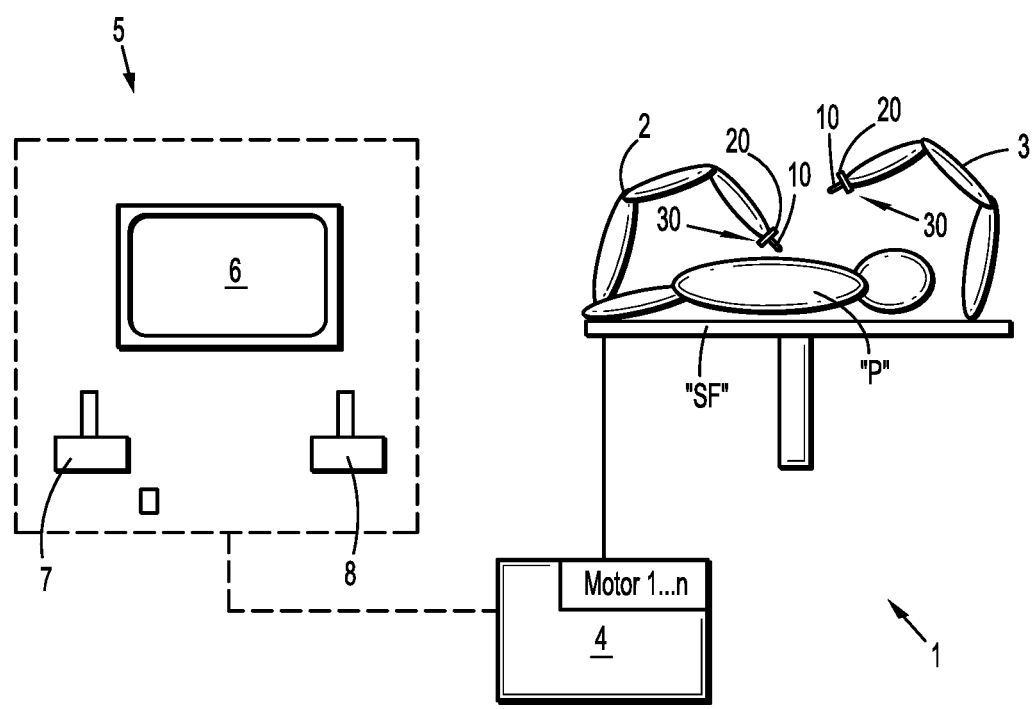
FIG. 1 is a schematic illustration of a robotic surgical system including a robotic surgical assembly in accordance with the present disclosure.

Embodiments of the presently disclosed robotic surgical system including an instrument adapter for interconnecting a drive mechanism and a surgical loading unit having an end effector, and methods thereof, are described in detail with reference to the drawings, in which like reference numerals designate identical or corresponding elements in each of the several views. As used herein the term "distal" refers to that portion of the robotic surgical system, instrument adapter, surgical loading unit, or component thereof that is further from the user, while the term "proximal" refers to that portion of the robotic surgical system, instrument adapter, surgical loading unit, or component thereof that is closer to the user.

Figure 2:
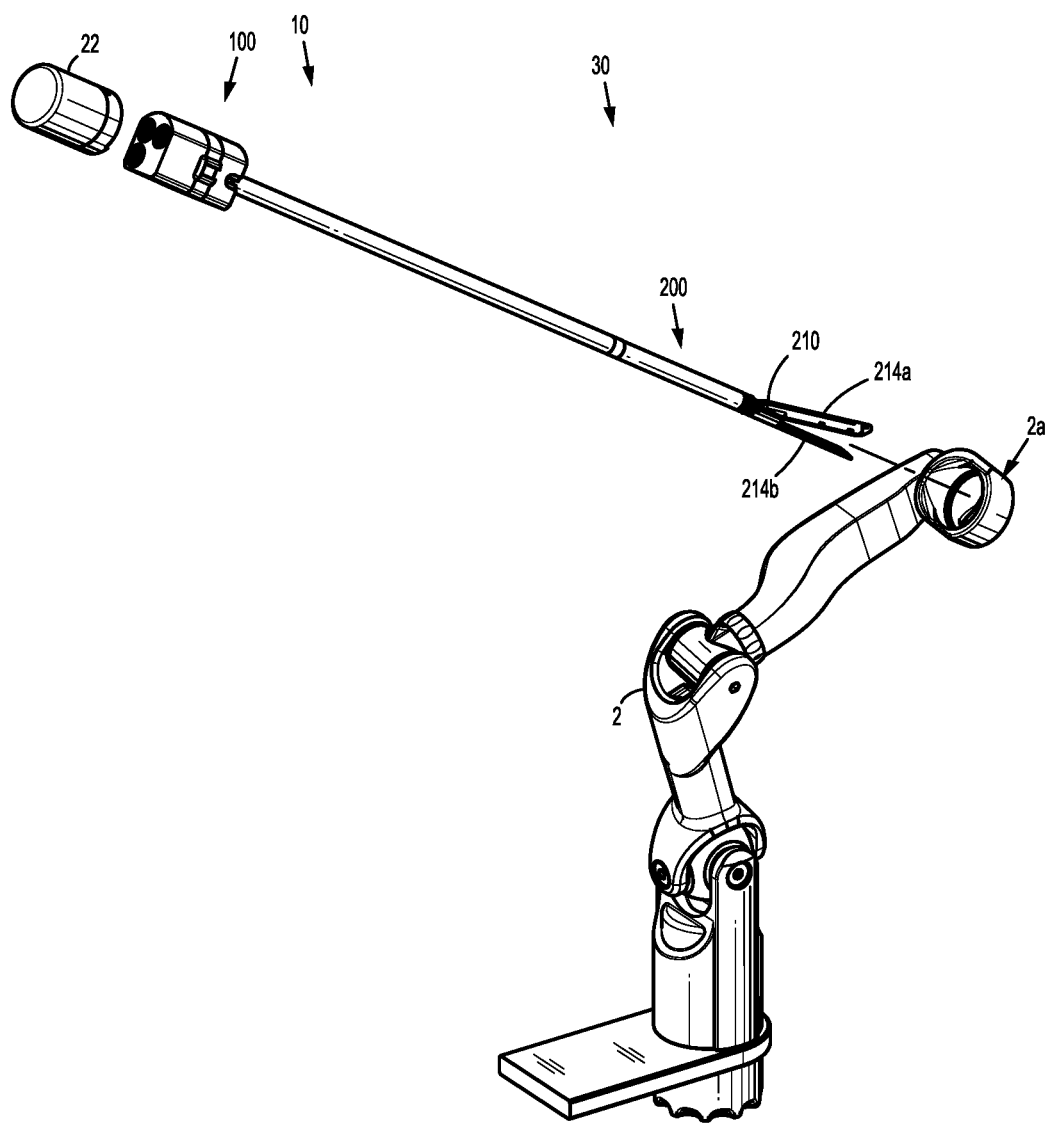
FIG. 2 is a perspective view of a surgical robotic arm of the robotic surgical assembly of FIG. 1 illustrating an electromechanical surgical instrument and a drive mechanism being attached to the surgical robotic arm.

Referring initially to FIGS. 1 and 2, a surgical system, such as, for example, a robotic surgical system 1, generally includes a plurality of surgical robotic arms 2, 3 having an electromechanical surgical instrument 10 removably attached thereto; a control device 4; and an operating console 5 coupled with control device 4.

With continued reference to FIG. 1, operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art. Each of the robotic arms 2, 3 may be composed of a plurality of members, which are connected through joints. Robotic arms 2, 3 may be driven by electric drives (not shown) that are connected to control device 4. Control device 4 (e.g., a computer) is set up to activate the drives, in particular by means of a computer program, in such a way that robotic arms 2, 3, their drive mechanisms 20, and thus electromechanical surgical instrument 10 (including end effector 210) execute a desired movement according to a movement defined by means of manual input devices 7, 8. Control device 4 may also be set up in such a way that it regulates the movement of robotic arms 2, 3 and/or of the drives.

Robotic surgical system 1 is configured for use on a patient "P" lying on a surgical table "ST" to be treated in a minimally invasive manner by means of a surgical instrument, e.g., electromechanical surgical instrument 10. Robotic surgical system 1 may also include more than two robotic arms 2, 3, the additional robotic arms likewise being connected to control device 4 and being telemanipulatable by means of operating console 5. A surgical instrument, for example, electromechanical surgical instrument 10 (including end effector 210), may also be attached to the additional robotic arm.

Control device 4 may control a plurality of motors (Motor 1 . . . n) with each motor configured to drive a relative rotation of drive members of an instrument adapter 100 (FIGS. 2-7B) of electromechanical surgical instrument 10 to effect operation and/or movement of each end effector 210 of electromechanical surgical instrument 10. It is contemplated that control device 4 coordinates the activation of the various motors (Motor 1 . . . n) to coordinate a clockwise or counter-clockwise rotation of drive members (not shown) of drive mechanism 22 in order to coordinate an operation and/or movement of a respective end effector 210. In embodiments, each motor can be configured to actuate a drive rod or a lever arm to effect operation and/or movement of each end effector 210 of electromechanical surgical instrument 10.

For a detailed discussion of the construction and operation of a robotic surgical system, reference may be made to U.S. Patent Application Publication No. 2012/0116416, filed on Nov. 3, 2011, entitled "Medical Workstation," the entire contents of which are incorporated herein by reference.

With specific reference to FIG. 2, robotic surgical system 1 includes a surgical assembly 30, which includes robotic arm 2, an electromechanical surgical instrument 10 configured to be coupled with or to robotic arm 2, and a drive mechanism or instrument drive unit 22 configured to be coupled to electromechanical surgical instrument 10. Instrument drive unit 22 is configured for powering electromechanical surgical instrument 10. Instrument drive unit 22 transfers power and actuation forces from its motors (not shown) to instrument adapter 100 of electromechanical surgical instrument 10 to ultimately drive movement of components of end effector 210, for example, a movement of a knife blade (not shown), which effects a closing and opening of jaw members 214a, 214b of end effector 210. Instrument drive unit 22 includes a plurality of driving members (not shown) attached to a respective motor (not shown) such that the drive members are independently rotatable with respect to one another.

Figure 3:
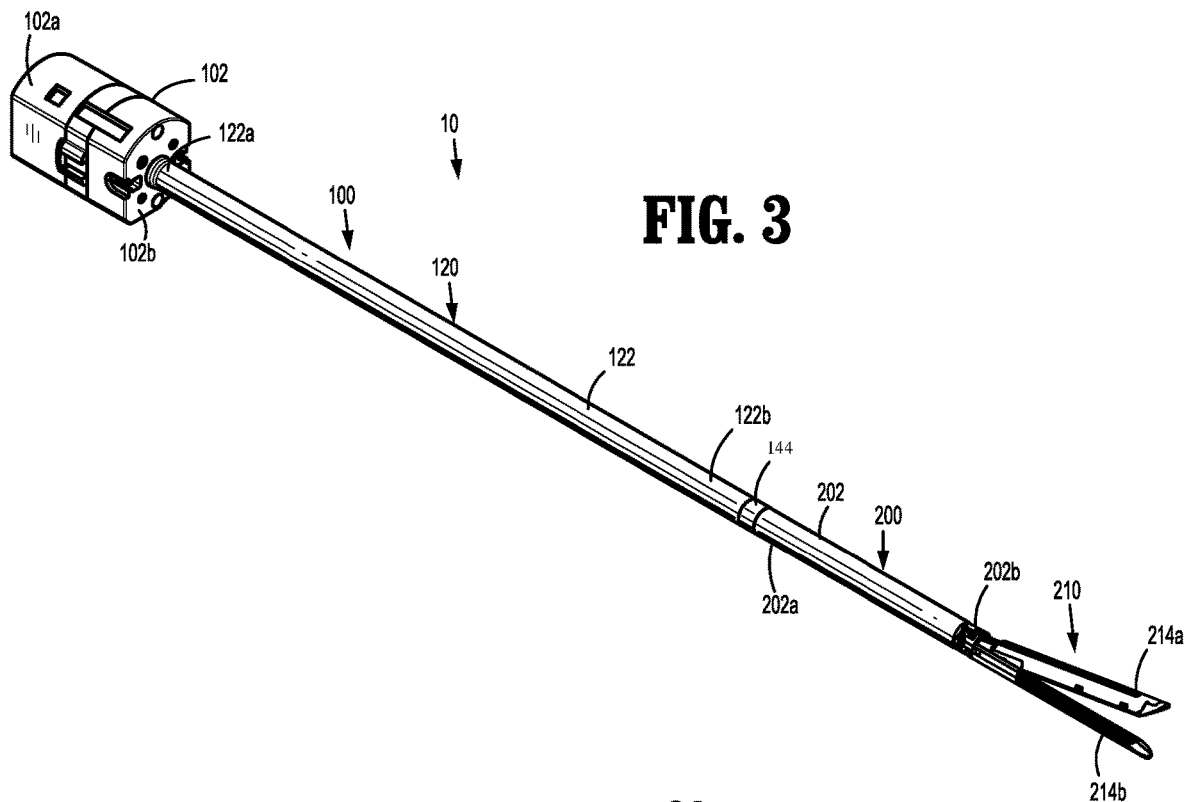
FIG. 3 is perspective view of the electromechanical surgical instrument of FIG. 2 including an instrument adapter having a surgical loading unit connected thereto.
Figure 4:
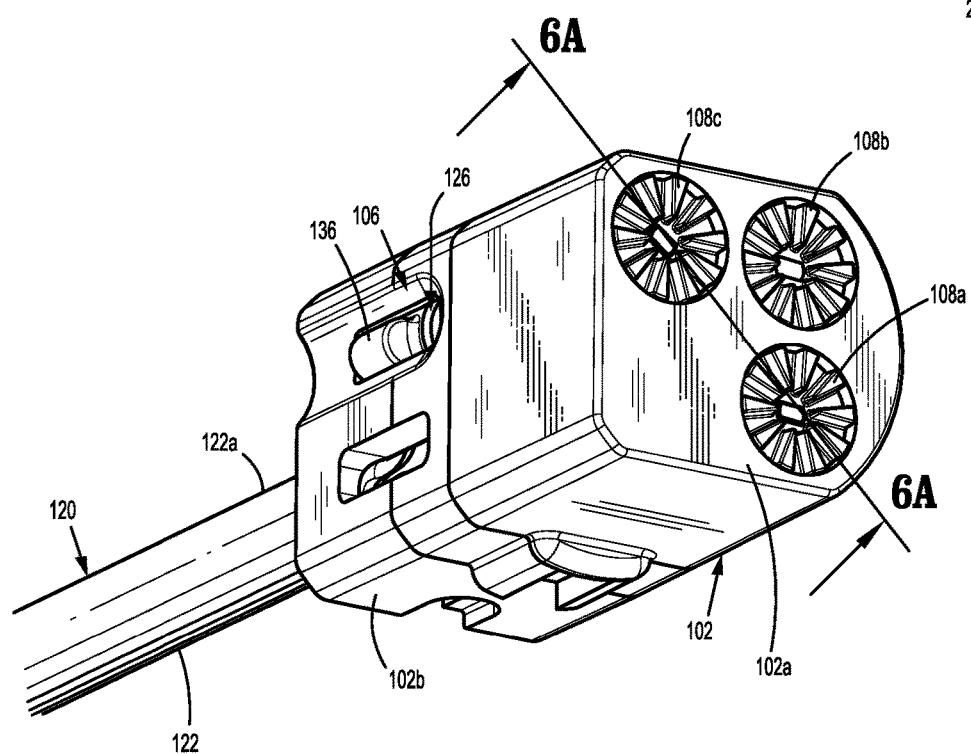
FIG. 4 is an enlarged view of the instrument adapter of FIG. 3 including a housing connected to a shaft assembly.

With reference to FIGS. 3 and 4, as mentioned above, electromechanical surgical instrument 10 generally includes an instrument adapter 100 and a surgical loading unit 200, which extends distally from instrument adapter 100. Instrument adapter 100 is configured to interconnect instrument drive unit 22 (FIG. 2) and surgical loading unit 200 to transfer actuation forces generated by instrument drive unit 22 to end effector 210 of surgical loading unit 200. Instrument adapter 100 includes a housing 102 and a shaft assembly 120 extending distally from within housing 102. Housing 102 of instrument adapter 100 has a generally cylindrical configuration and includes a proximal end 102a and a distal end 102b. In embodiments, housing 102 may be any shape suitable for receipt in or attachment to a distal end 2a (FIG. 2) of robotic arm 2. Housing 102 defines a cavity (not explicitly shown) therein that houses various components of instrument adapter 100. Housing 102 defines a window 106 in a side surface thereof. A nut 126 is disposed adjacent to window 106 and accessible therethrough by a clinician to manually manipulate nut 126, as will be described in greater detail below.

Proximal end 102a of housing 102 of instrument adapter 100 supports a first, a second, and a third input drive coupler 108a, 108b, 108c, respectively, configured to be detachably, non-rotatably coupled to one respective drive member (not shown) of instrument drive unit 22. Housing 102 includes a first, a second, and a third drive member 112, 114, 116, each being disposed within housing 102 and extending between proximal end 102a and distal end 102b of housing 102. In some embodiments, housing 102 may include fewer or more than three drive members.

A proximal end 112a of first drive member 112 is non-rotatably coupled to first input drive coupler 108a, and a distal end 112b of first drive member 112 is operatively coupled to an articulation link 170 to actuate an articulation of end effector 210. A proximal end 114a of second drive member 114 is non-rotatably coupled to second input drive coupler 108b, and a distal end (not shown) of second drive member 114 is operatively coupled to a firing rod 124 configured to actuate movement of a knife blade (not shown) of surgical loading unit 200 and a movement of jaw members 214a, 214b, for example. A proximal end 116a of third drive member 116 is non-rotatably coupled to third input drive coupler 108c, and a distal end 116b of third drive member 116 is operatively coupled to a locking link 150, via a locking nut 126, for selectively locking surgical loading unit 200 to instrument adapter 100, as will be described in detail below. As such, upon actuation of motors (not shown) of instrument drive unit 22, the drive members (not shown) of instrument drive unit 22 are rotated, resulting in concomitant rotation of first, second, and third drive members 112, 114, 116, respectively, of instrument adapter 100 via the respective first, second, and third input drive couplers 108a, 108b, 108c of housing 102.

Figure 5:
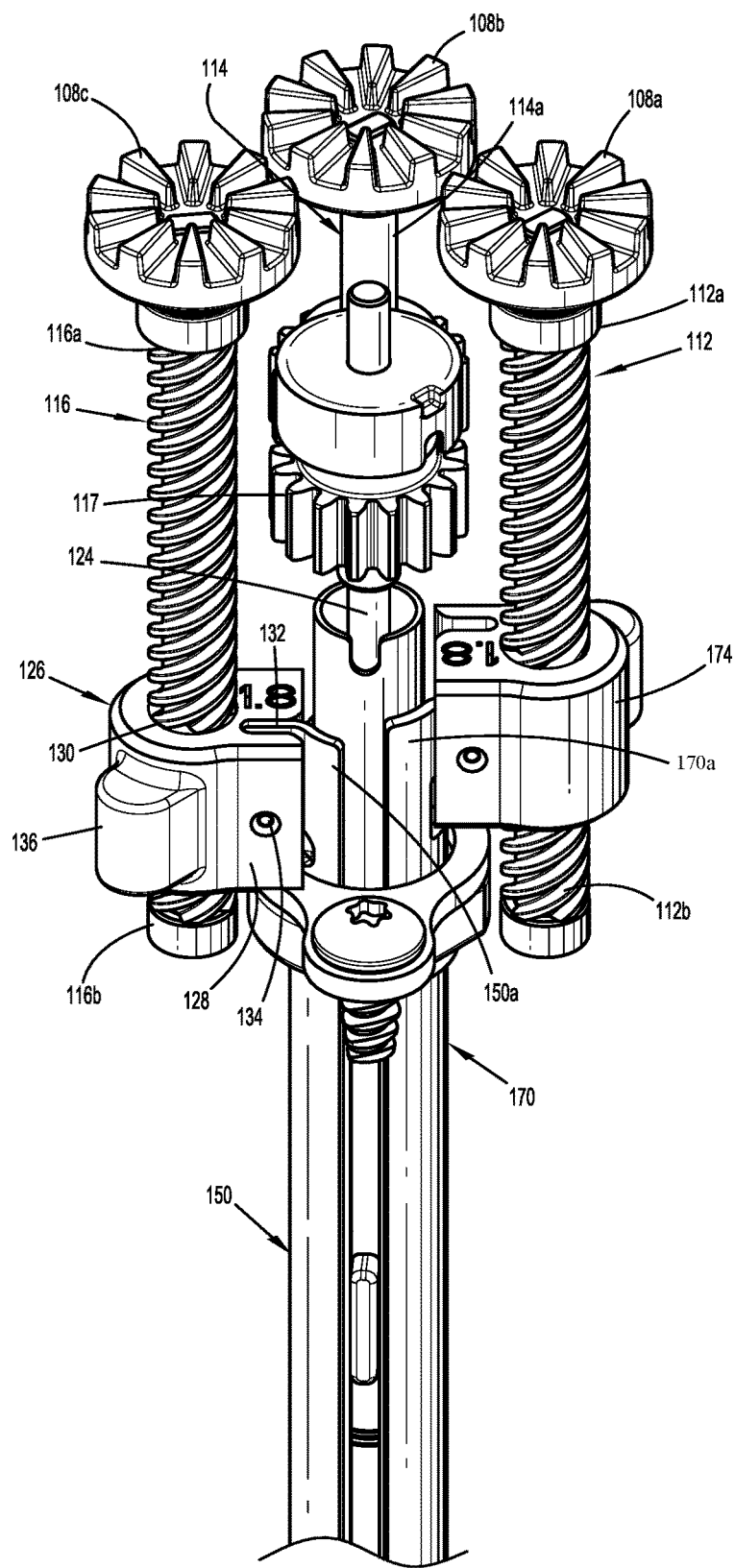
FIG. 5 is a perspective view, with parts removed, of internal parts of the housing and shaft assembly of the instrument adapter of FIGS. 3 and 4.
Figure 6A:
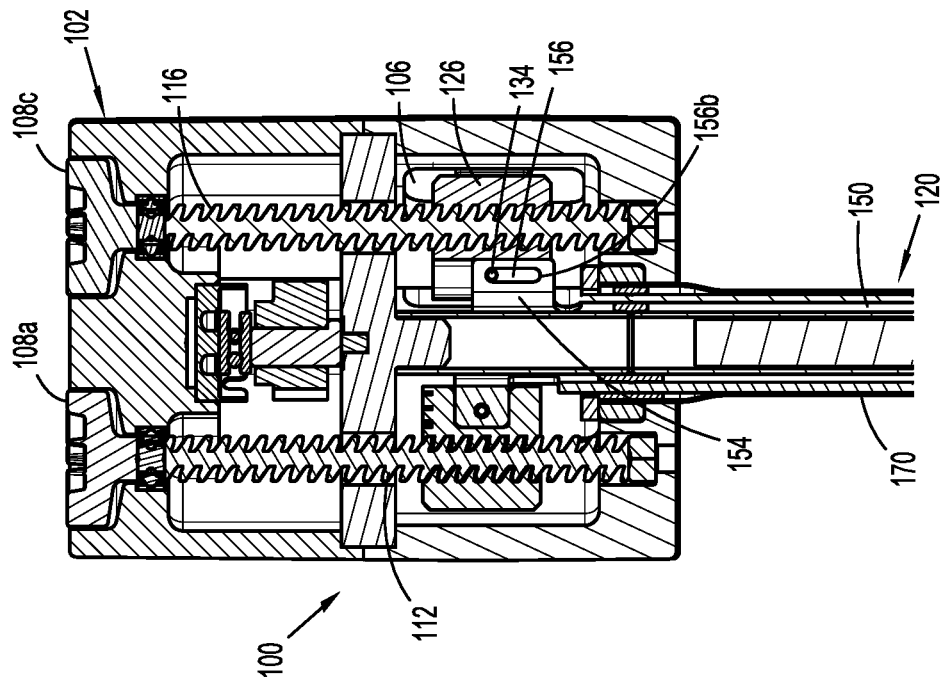
FIG. 6A is a cross sectional view, taken along line 6A-6A, of the instrument adapter of FIG. 4 illustrating a nut of the instrument adapter in a locking position along a drive member.
Figure 6B:
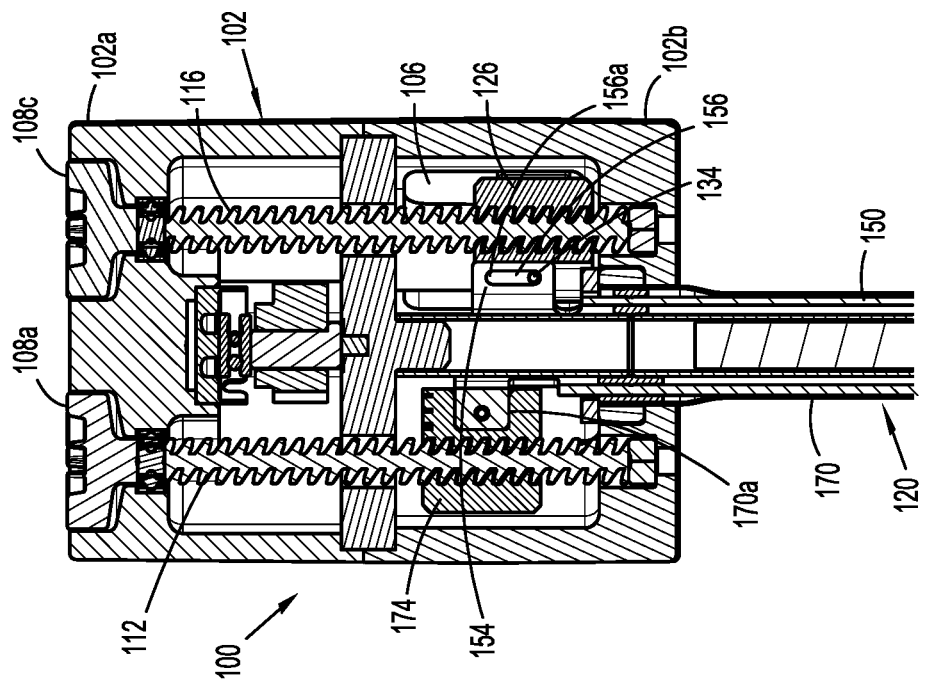
FIG. 6B is a cross sectional view, taken along line 6A-6A, of the instrument adapter of FIG. 4 illustrating the nut of the instrument adapter in a non-locking position along the drive member.

With reference to FIGS. 5-6B, housing of instrument adapter 100 further includes a pair of shrouds, locks, or the like, such as, for example, a locking nut 126 and a nut 174. Locking nut 126 is threadedly coupled to third drive member 116 and axially movable relative thereto. Nut 126 has a body 128 defining a lumen 130 longitudinally therethrough configured for receipt of a threaded portion of third drive member 116. An internal surface of lumen 130 is threaded. An external surface of nut 126 is keyed to internal architecture of housing 102 (e.g., a longitudinally extending slot or channel) such that rotation of third drive member 116 effects either proximal or distal movement of nut 126 along drive member 116. Body 128 of nut 126 has a slit 132 defined therein for receipt and securement of a proximal end 150a of locking link 150. Nut 126 has a projection or rod 134 extending transversely through slit 132 and at least into proximal end 150a of locking link 150 to retain locking link 150 within slit 132 of nut 126. Rod 134 is movably disposed within a longitudinal slot 156 formed in proximal end 150a of link 150, as will be described in greater detail below. Nut 126 further includes a tab 136 extending laterally from body 128 thereof. Tab 136 is disposed adjacent window 106 of housing 102 for manual movement of nut 126 by a clinician (if needed), as will be described in greater detail below. Nut 174 is similar to nut 126. Nut 174 is threadedly coupled to first drive member 112 and slidable therealong upon rotation of first drive member 112.

With reference to FIGS. 3, 4, and 5, as mentioned above, instrument adapter 100 includes a shaft assembly 120. Shaft assembly 120 extends distally from housing 102, is at least partially disposed within housing 102, and operatively intercouples drive members 112, 114, 116 of instrument adapter 100 with surgical loading unit 200. Shaft assembly 120 generally includes a shaft or outer tube 122, in which a firing rod or actuation bar 124, a locking link 150, and an articulation link 170 are disposed. Shaft 122 has a proximal end 122a and a distal end 122b. Proximal end 122a of shaft 122 is coupled to and extends within housing 102. Distal end 122b of shaft 122 is configured to be operably coupled to an elongate portion 202 of surgical loading unit 200.

Figure 7B:
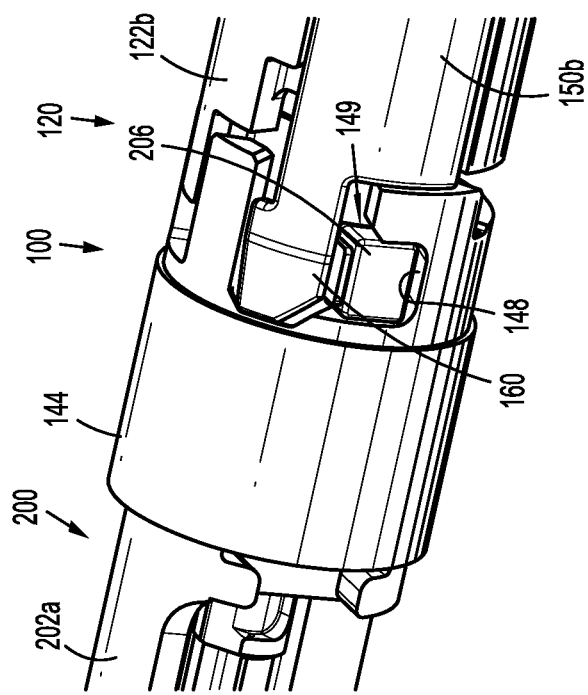
FIG. 7B is a perspective view of the distal end of the instrument adapter of FIG. 4 coupled to the surgical loading unit, illustrating the link of the instrument adapter in a distal locking position for locking the surgical loading unit to the instrument adapter.
Figure 7A:
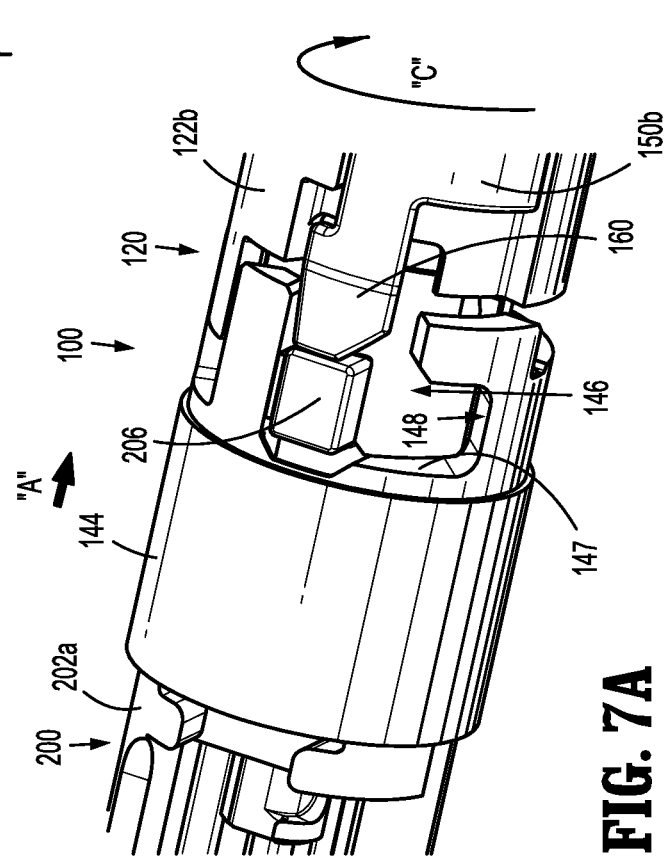
FIG. 7A is a perspective view of a distal end of the instrument adapter of FIG. 4 coupled to a surgical loading unit, illustrating a link of the instrument adapter in a proximal non-locking position for loading the surgical loading unit with the instrument adapter.

With brief reference to FIGS. 7A and 7B, distal end 122b of shaft 122 includes a cap 144 configured for receipt of a proximal end 202a of surgical loading unit 200. Cap 144 defines a cutout 146 in a proximal end thereof. Cutout 146 is configured for receipt of an extension 160 of locking link 150, as will be described in greater detail below. Cutout 146 has an inner groove 148 configured for disposal of a lug 206 of surgical loading unit 200.

With reference to FIGS. 5, 6A, and 6B, locking link 150 of shaft assembly 120 of instrument adapter 100 is longitudinally movable within shaft 122 of shaft assembly 120 between a proximal non-locking position or unblock position, and a distal locking position or block position. Locking link 150 is resiliently biased toward the distal locking position by a biasing member or spring. Locking link 150 has a proximal end 150a and a distal end 150b (FIGS. 7A and 7B). Proximal end 150a of locking link 150 is disposed within housing 102, and distal end 150b of locking link 150 is disposed within shaft 122. Proximal end 150a of link 150 has a laterally extending wing 154 movably disposed within slit 132 of nut 126. Wing 154 of proximal end 150a of locking link 150 includes a longitudinal slot 156 formed therein. As briefly described above, rod 134 of nut 126 is disposed within longitudinal slot 156 of locking link 150 and rides within longitudinal slot 156 upon proximal or distal longitudinal movement of locking link 150 relative to nut 126.

Longitudinal slot 156 of locking link 150 has a proximal end surface 156a and a distal end surface 156b. As such, when nut 126 is in a first, distal position, as shown in FIG. 6A, rod 134 of nut 126 is engaged with distal end surface 156b of longitudinal slot 156 of locking link 150 resisting or preventing locking link 150 from moving in a proximal direction from the distal locking position to the proximal non-locking position. When nut 126 is in a second, proximal position, as shown in FIG. 6B, rod 134 of nut 126 is disengaged from distal end surface 156b of longitudinal slot 156 of locking link 150 so as to no longer resist locking link 150 from moving in a proximal direction from the distal locking position to the proximal non-locking position.

With brief reference to FIGS. 7A and 7B, distal end 150b of locking link 150 of instrument adapter 100 is disposed within cutout 146 of cap 144 of shaft 122 for selectively locking surgical loading unit 200 to instrument adapter 100, as will be described in greater detail below. Distal end 150b of locking link 150 includes an extension 160 configured for locking engagement with lug 206 of surgical loading unit 200 upon axial insertion and rotation of surgical loading unit 200 into shaft assembly 120, as will be described in greater detail below. When locking link 150 is in the proximal non-locking position or unblock position, as shown in FIG. 7A, extension 160 of locking link 150 is proximally spaced from an end surface 147 of distal cap 144 such that lug 206 of surgical loading unit 200 can be inserted within cutout 146 of distal cap 144 and rotated therein. When locking link 150 is in the distal locking position or block position, as shown in FIG. 7B, extension 160 of locking link 150 is engaged to end surface 147 of distal cap 144 such that extension 160 of locking link 150 and cutout 146 of cap 144 cooperatively define an enclosure 149 for retaining lug 126 therein to lock surgical loading unit 200 with instrument adapter 100.

With continued reference to FIGS. 5, 6A, and 6B, as mentioned above, shaft assembly 120 further includes an articulation link 170. Articulation link 170 has a proximal end 170a and a distal end (not shown). Proximal end 170a of articulation link 170 is disposed within shaft 122 of shaft assembly 120 and is fixed with nut 174 of instrument adapter 100. As such, upon rotation of first drive member 112, first nut 174 moves either proximally or distally along first drive member 112 to effect a corresponding longitudinal movement of articulation link 170. The distal end of articulation link 170 may be pinned to a proximal end of end effector 210 to articulate end effector 210 relative to distal end 202b of tube 202 of surgical loading unit 200.

The firing rod 124 is operatively coupled to the distal end (not shown) of second drive member 114 via a plurality of intermeshed gears 117. Gears 117 are coupled to firing rod 124 such that rotation of gears 117 results in axial translation of firing rod 124 relative thereto. As such, rotation of second drive member 114 axially translates firing rod 124 to effect an actuation of end effector 210.

With reference to FIGS. 3, 7A, and 7B, as mentioned above, electromechanical surgical instrument 10 includes a surgical loading unit 200 that is selectively attachable to instrument adapter 100 and actuatable by instrument adapter 100. Surgical loading unit 200 may be a single use loading unit that is disposable, or a multiple use loading unit that can be sterilized for reuse. Surgical loading unit 200 generally includes an elongate portion 202 and an end effector 210. Elongate portion 202 may be tubular and has a proximal end 202a configured to be coupled to distal end 122b of shaft 122 of instrument adapter 100, and a distal end 202b having end effector 210 attached thereto. Proximal end 202a of elongate portion 202 has a protrusion or lug 206 (FIGS. 7A and 7B) extending laterally therefrom. Lug 206 of elongate portion 202 is configured to be axially passed through distal cap 144 of shaft 122 of instrument adapter 100, into cutout 146 of distal cap 144, and rotated into inner groove 148 of cutout 146 to selectively lockingly couple surgical loading unit 200 with instrument adapter 100.

End effector 210 of surgical loading unit 200 extends from distal end 202b of elongate portion 202 of surgical loading unit 200. It is contemplated that end effector 210 may be directly coupled to instrument adapter 100 rather than be directly coupled to elongate portion 202 of surgical loading unit 200. End effector 210 generally includes a pair of opposing jaw members 214a, 214b. End effector 210 may be moved, by firing rod 124 of instrument adapter 100, from an open configuration wherein tissue (not shown) is received between jaw members 214a, 214b, and a closed configuration wherein the tissue is clamped between and treated by jaw members 214a, 214b.

In use, with reference to FIGS. 6A, 6B, 7A, and 7B, to load surgical loading unit 200 onto instrument adapter 100, instrument adapter 100 is switched (either manually or automatically) to a loading state, in which locking link 150 of instrument adapter 100 is free to move from the distal locking position, to the proximal non-locking position. In particular, the third drive member (not shown) of instrument drive unit 22 is manually or automatically activated to drive rotation of third drive member 116 of instrument adapter 100 via third input drive coupler 108c. Rotation of third drive member 116 longitudinally moves nut 126 proximally along third drive member 116 from the distal position, shown in FIG. 6A, to the proximal position, shown in FIG. 6B. As nut 126 moves proximally along third drive member 116, rod 134 of nut 126 moves longitudinally through longitudinal slot 156 of proximal end 150a of locking link 150 to disengage from distal end surface 156b of longitudinal slot 156 of locking link 150.

With nut 126 in the proximal position and rod 134 of nut 126 out of engagement with distal end surface 156b of longitudinal slot 156 of locking link 150, rod 134 of nut 126 no longer resists proximal longitudinal movement of locking link 150. As such, an application of a force on extension 160 of locking link 150 by lug 206 of surgical loading unit 200, in a proximal direction, indicated by arrow "A" in FIG. 7A, effects proximal longitudinal movement of locking link 150 to move locking link 150 from the distal locking position, shown in FIG. 7B, to the proximal non-locking position, shown in FIG. 7A.

To lockingly couple surgical loading unit 200 with instrument adapter 100, surgical loading unit 200 is then rotated, in a direction indicated by arrow "B" in FIG. 7B, to position lug 206 of surgical loading unit 200 within inner groove 148 of cap 144 of shaft assembly 120. Upon rotating lug 206 of surgical loading unit 200 into inner groove 148, the distal resilient bias of locking link 150 causes locking link 150 to move distally relative to shaft 122 to position locking link 150 in the distal locking position, in which extension 160 of locking link 150 prevents lug 206 from rotating out of enclosure 149. As such, surgical loading unit 200 is lockingly coupled to instrument adapter 100 and ready for use.

Once surgical loading unit 200 is coupled to instrument adapter 100, it may be beneficial to prevent inadvertent removal of surgical loading unit 200 from instrument adapter 100. To prevent this, instrument adapter 100 may be switched from the loading state to a locking state. In some embodiments, a clinician, upon successfully coupling surgical loading unit 200 to instrument adapter 100, may activate instrument drive unit 22 to switch instrument adapter 100 to the locking state. Alternately, it is envisioned that a computer, for example control device 4 (FIG. 1) may be programmed to automatically activate instrument drive unit 22 to switch instrument adapter 100 to the locking state upon control device 4 detecting that surgical loading unit 200 is successfully coupled to instrument adapter 100. It is further contemplated that surgical system 1 may be configured to automatically switch instrument adapter 100 to the locking state upon detecting that end effector 210 is disposed adjacent a patient or upon end effector 210 entering an access port (not shown) that provides access to a surgical site within the patient. In some embodiments, surgical system 1 may be configured to inhibit passage of jaw members 214a, 214b of end effector 200 into or through the access port (not shown) unless surgical loading unit 200 is fully and property connected and/or locked to shaft assembly 120. Specifically, if a lock or connection switch (not shown) is not activated by locking link 150 during the connection of surgical loading unit 200 to shaft assembly 120, and/or if articulation link 170 is prevented from moving to a load position, upon an incomplete connection of surgical loading unit 200 to shaft assembly 120, surgical system 1 may inhibit or prevent advancement of electromechanical surgical instrument 10, and thus jaw members 214a, 214b of end effector 200, into or through the access port.

To switch instrument adapter 100 to the locking state, thereby locking surgical loading unit 200 thereto, nut 126 of instrument adapter 100 is moved to the distal locking position (FIG. 6A). In the distal locking position, nut 126 resists proximal longitudinal movement of locking link 150 from the distal locking position (FIG. 7B) to the proximal non-locking position (FIG. 7A), in which the surgical loading unit 200 may be inadvertently removed from instrument adapter 100. In this situation, nut 126 acts as a lock by preventing link 150 from moving and thereby preventing removal of surgical loading unit 200 from the instrument adapter 100. To move nut 126 to the distal locking position, the third drive member (not shown) of instrument drive unit 22 is activated (either manually or automatically) to drive rotation of third drive member 116 of instrument adapter 100 via third input drive coupler 108c. Rotation of third drive member 116 longitudinally moves nut 126 distally along third drive member 116 from the proximal position, shown in FIG. 6B, to the distal position, shown in FIG. 6A. As nut 126 moves distally along third drive member 116, rod 134 of nut 126 moves longitudinally through longitudinal slot 156 of proximal end 150a of locking link 150 and into engagement with distal end surface 156b of longitudinal slot 156 of locking link 150.

With nut 126 in the distal position, and rod 134 of nut 126 engaged with distal end surface 156b of longitudinal slot 156 of locking link 150, rod 134 of nut 126 resists proximal longitudinal movement of locking link 150. As such, inadvertent application of a force on locking link 150, in a proximal direction indicated by arrow "A" in FIG. 7A, will not move locking link 150 out of the distal locking position, shown in FIG. 7B, and into the proximal non-locking position, shown in FIG. 7A.

To remove surgical loading unit 200 from instrument adapter 100, instrument adapter 100 is switched from the locking state to an unloading state. In the unloading state, nut 126 is disposed in a third position along third drive member 116, located proximally of the first and second positions of nut 126 described above. To move nut 126 to the third position, the third drive member (not shown) of instrument drive unit 22 is activated (either automatically or manually) to drive rotation of third drive member 116 of instrument adapter 100 via third input drive coupler 108c. Rotation of third drive member 116 longitudinally moves nut 126 proximally along third drive member 116 from the distal position, shown in FIG. 6A, to the third position (not shown), located proximally of the distal position, shown in FIG. 6A. As nut 126 moves proximally along third drive member 116, rod 134 of nut 126 moves longitudinally through longitudinal slot 156 of proximal end 150a of locking link 150 to ultimately engage with proximal end surface 156a of longitudinal slot 156 of locking link 150. Upon continued proximal movement of nut 126 along third drive member 116, rod 134 of nut 126 drives proximal movement of locking link 150 from the distal locking position of FIG. 7B to the proximal non-locking position of FIG. 7A.

With locking link 150 in the proximal non-locking position, as shown in FIG. 7A, surgical loading unit 200 may be detached from instrument adapter 100 since lug 206 of surgical loading unit 200 is no longer captured between inner groove 148 of cap 144 and extension 160 of locking link 150. To remove surgical loading unit 200 from instrument adapter 100, surgical loading unit 200 is rotated, in a direction indicated by arrow "C" in FIG. 7B, to position lug 206 of surgical loading unit 200 out of inner groove 148 of cap 144 of shaft assembly 120. Surgical loading unit 200 is then axially moved in a distal direction out of engagement with instrument adapter 100. As such, surgical loading unit 200 may be cleaned for reuse, or another surgical loading unit may be exchanged.

In some embodiments, nut 126 may be automatically moved to the third position upon surgical system 1 detecting that end effector 210 of surgical loading unit 200 is no longer disposed within the access port or when end effector 210 is a predetermined distance from the patient.

In some embodiments, a situation may arise in which instrument drive unit 22 is not able to switch instrument adapter 100 from the locking state to the unloading state such that surgical loading unit 200 cannot be removed from instrument adapter 100 via instrument drive unit 22 and must be done so manually. In this situation, to remove surgical loading unit 200 from instrument adapter 100, instrument drive unit 22 is first detached from housing 102 of instrument adapter 100. A clinician may then manually move tab 136 of nut 126 in a proximal direction by applying a threshold amount of force to tab 136. It can be appreciated that because nut 126 is threadedly engaged to drive member 116, it cannot move therealong without being rotated. However, drive member 116 may be axially movable in a proximal direction relative to housing 102 when instrument drive unit 22 is not engaged to housing 102. Accordingly, as a clinician applies a proximally-oriented force on nut 126, drive member 116 moves in a proximal direction with nut 126 to allow nut 126 to be manually moved to the proximal non-locking position.

As nut 126 is manually moved in a proximal direction, rod 134 of nut 126 engages proximal end surface 156a of longitudinal slot 156 of locking link 150, moving locking link 150 in the proximal direction into the proximal non-locking position. With locking link 150 in the proximal non-locking position, surgical loading unit 200 may be removed by rotating surgical loading unit 200 in the direction indicated by arrow "C" in FIG. 7B, and then moving surgical loading unit 200 in a distal direction out of cap 144 of instrument adapter 100.

By providing surgical system 1 with the ability to selectively lock surgical loading unit 200 with instrument adapter 100, any possibility of releasing or dropping surgical loading unit 200 is removed. The locking state of instrument adapter 100 may also be used when surgical system 1 is calibrating instrument adapter 100 prior to connecting surgical loading unit 200 thereto to prevent a user from loading a surgical loading unit 200 into instrument adapter 100 mid-calibration and causing surgical system 1 to incorrectly calibrate.

In some embodiments, various components of instrument adapter 100 may be calibrated prior to usage. For example, to calibrate locking link 150 of instrument adapter 100, locking link 150 is moved distally until proximal end surface 156a of slot 156 of locking link 150 engages rod 134 of nut 126 such that locking link 150 is in a distal-most position thereof. Locking link 150 is then moved proximally a nominal distance (e.g., approximately 0.005 inches) to a home position. Locking link 150 is then moved proximally from the home position to a proximal non-locking position, as shown in FIG. 7A. Upon moving locking link 150 to the proximal non-locking position, instrument adapter 100 may be monitored for an unexpected amount of torque exerted by a motor of instrument drive unit 22 (e.g., a spike or excessive load in a value of a torque cell) that would indicate a failed calibration of locking link 150. After locking link 150 is moved to the proximal non-locking position, locking link 150 is then moved distally back to the home position and held in the home position for calibration of both firing rod 124 and articulation link 170, as will be described below.

During use of instrument adapter 100, locking link 150 will be actuated using position control, and torque will be monitored continuously during motion to detect a fault state in which the torque required to move locking link 150 is beyond a threshold amount (e.g., a spike or excessive load in value of a torque cell).

As described in detail above, articulation link 170 of instrument adapter 100 effects articulation of end effector 210 relative to elongate portion 202 of surgical loading unit 20. To calibrate articulation link 170 of instrument adapter 100, while holding locking link 150 in the home position, articulation link 170 is moved proximally to a proximal-most position in which articulation link 170 reaches a hard stop. A measurement is taken of the torque being exerted by a motor of instrument drive unit 22 when articulation link 170 reaches the hard stop and is compared to normal operating torques of the motors of instrument drive unit 22. Articulation link 170 is then moved distally a known distance to a non-articulated position that corresponds to end effector 210 being in alignment with (i.e., parallel) elongate portion 202 of surgical loading unit 200. A measurement is taken of the torque being exerted by a motor of instrument drive unit 22 when articulation link 170 is moved through non-articulated positions.

Actuation bar 124 of instrument adapter 100 may also be calibrated. As described in detail above, actuation bar 124 effects both the longitudinal movement of the knife blade (not explicitly shown) and the closing of jaw members 214a, 214b of end effector 210. To calibrate actuation bar 124, actuation bar 124 is moved proximally until actuation bar 124 reaches a hard stop, and thus cannot be further moved proximally. A measurement is taken of the torque being exerted by a motor of instrument drive unit 22 when actuation bar 124 reaches the hard stop and compared to normal operating torques of the motors of instrument drive unit 22. After actuation bar 124 reaches the hard stop, actuation bar 124 is moved distally about 1.38 mm to a home position from the hard stop.

In accordance with the present disclosure, during the entire calibration sequence, locking link 150 has been held in the distal locking position shown in FIG. 7B.

After the above-noted calibration sequence has been conducted, instrument adapter 100 is ready for use.

In some embodiments, an array of lights may be provided any or all of the components of surgical robotic assembly 30, such as, for example, the surgical robotic arm 2, the instrument drive unit 22, and/or the instrument adapter 100. These lights may indicate the status of the surgical instrument, for example: the robotic arm is in patient with no errors (ready to retract for exchange of the surgical loading unit); the robotic arm is in the patient with an error (cannot retract the surgical loading unit); or the robotic arm is out of the patient and in an unlocked state, a locked state, a loading state waiting for the surgical loading unit, a loading state having successfully loaded the surgical loading unit, or an unloaded state having mis-loaded the surgical loading unit.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An instrument adapter detachably couplable to an instrument drive unit and an end effector, the instrument adapter comprising:
   a drive member coupled to an output of the instrument drive unit when the instrument adapter is coupled to the instrument drive unit;
   a shaft having a coupling interface corresponding to that of the end effector;
   a link movable between a block position in which the link prevents attaching or detaching of the end effector to the shaft through the coupling interface and an unblock position in which the link does not prevent said attaching or detaching; and
   a lock driven by the drive member and coupled to the link, the lock drivable to a plurality of states including:
      a first state in which the link is driven to the unblock position;
      a second state in which the lock is driven to a position in which the link is manually movable in at least one direction between the block and unblock positions; and
      a third state in which the link is driven to the block position.

2. The instrument adapter of claim 1, further comprising a housing, the drive member and the lock disposed within the housing.

3. The instrument adapter of claim 2, wherein the link includes a proximal end disposed within the housing and a distal end disposed within the shaft.

4. The instrument adapter of claim 1, wherein the lock is threadably coupled to the drive member and axially movable relative thereto.

5. The instrument adapter of claim 1, wherein a proximal end of the link is coupled to the lock and slidable relative thereto.

6. The instrument adapter of claim 1, wherein a proximal end of the link includes a laterally extending wing movably disposed within a slit of the lock.

7. The instrument adapter of claim 6, wherein the wing of the link includes a longitudinal slot, and the lock includes a rod disposed within the longitudinal slot and movable therein upon longitudinal movement of the link relative to the lock.

8. The instrument adapter of claim 7, wherein the longitudinal slot of the link includes a proximal end surface and a distal end surface, and when the lock is in the third state, the rod of the lock is engaged with the distal end surface of the longitudinal slot, and when the lock is in the first or second states, the rod of the lock is disengaged from the distal end surface of the longitudinal slot.

9. The instrument adapter of claim 1, wherein the link is resiliently biased towards the block position.

10. The instrument adapter of claim 1, wherein a distal end of the link includes an extension, and a distal end of the shaft includes a cap defining a cutout configured for receipt of the extension of the link, and when the link is in the unblock position, the extension is spaced from an end surface of the cap, and when the link is in the block position, the extension engages the end surface of the cap.

11. An instrument adapter detachably couplable to an instrument drive unit and an end effector, the instrument adapter comprising:
   a drive member configured to be coupled to an output of an instrument drive unit;
   a shaft having a distal end configured to be coupled to an end effector;
   a link movable between a block position in which the link prevents attaching or detaching of an end effector to the distal end of the shaft and an unblock position in which the link does not prevent attaching or detaching of an end effector to the distal end of the shaft; and
   a lock driven by the drive member and coupled to the link, the lock drivable by the drive member between a plurality of states including: a first state in which the link is in the unblock position, a second state in which the lock is in a position in which the link is manually movable in at least one direction between the block and unblock positions, and a third state in which the link is in the block position.

12. The instrument adapter of claim 11, further comprising a housing, the drive member and the lock disposed within the housing.

13. The instrument adapter of claim 12, wherein the link includes a proximal end disposed within the housing and a distal end disposed within the shaft.

14. The instrument adapter of claim 11, wherein the lock is threadably coupled to the drive member and axially movable relative thereto.

15. The instrument adapter of claim 11, wherein a proximal end of the link is coupled to the lock and slidable relative thereto.

16. The instrument adapter of claim 11, wherein a proximal end of the link includes a laterally extending wing movably disposed within a slit of the lock.

17. The instrument adapter of claim 16, wherein the wing of the link includes a longitudinal slot, and the lock includes a rod disposed within the longitudinal slot and movable therein upon longitudinal movement of the link relative to the lock.

18. The instrument adapter of claim 17, wherein the longitudinal slot of the link includes a proximal end surface and a distal end surface, and when the lock is in the third state, the rod of the lock is engaged with the distal end surface of the longitudinal slot, and when the lock is in the first or second states, the rod of the lock is disengaged from the distal end surface of the longitudinal slot.

19. The instrument adapter of claim 11, wherein the link is resiliently biased towards the block position.

20. The instrument adapter of claim 11, wherein a distal end of the link includes an extension, and a distal end of the shaft includes a cap defining a cutout configured for receipt of the extension of the link, and when the link is in the unblock position, the extension is spaced from an end surface of the cap, and when the link is in the block position, the extension engages the end surface of the cap.

* * * * *